United States Patent [19]

Zabransky

[11] 3,948,603
[45] Apr. 6, 1976

[54] CONTROL SYSTEM FOR HF ALKYLATION

[75] Inventor: Robert F. Zabransky, Oak Brook, Ill.

[73] Assignee: Universal Oil Products Company, Des Plaines, Ill.

[22] Filed: May 10, 1974

[21] Appl. No.: 468,955

[52] U.S. Cl......... 23/253 A; 23/230 A; 235/151.12; 260/683.48
[51] Int. Cl.²..................... G01N 31/00; C07L 3/12
[58] Field of Search.......... 23/253 A, 230 A, 253 R; 208/DIG. 1; 235/151.12; 260/683.48

[56] References Cited
UNITED STATES PATENTS

| | | | |
|---|---|---|---|
| 3,000,812 | 9/1961 | Boyd, Jr. | 23/253 A X |
| 3,458,691 | 7/1969 | Boyd, Jr. | 23/253 A X |
| 3,497,449 | 2/1970 | Urban | 23/253 A X |
| 3,560,587 | 2/1971 | Borst, Jr. | 260/683.48 |
| 3,649,202 | 3/1972 | Bajek et al. | 23/253 A |
| 3,748,448 | 7/1973 | Sayles et al. | 235/151.12 |
| 3,751,229 | 8/1973 | Bajek et al. | 23/253 A |
| 3,755,492 | 8/1973 | Anderson | 260/683.48 |
| 3,760,168 | 9/1973 | Boyd | 235/151.12 |
| 3,778,603 | 12/1973 | Sweeney, Jr. | 235/151.12 |
| 3,814,916 | 6/1974 | Sweeney, Jr. | 235/151.12 |

Primary Examiner—Joseph Scovronek
Assistant Examiner—Arnold Turk
Attorney, Agent, or Firm—James R. Hoatson, Jr.; Robert W. Erickson; William H. Page, II

[57] ABSTRACT

A control system for regulating the reaction zone temperature in a process for the acid-catalyzed alkylation of an isoparaffin with an olefinic feed stream containing mixed olefins. The reaction zone temperature is adjusted to obtain the optimum for a given feed composition, in order to maximize the octane rating of the ultimate normally liquid alkylate product. The control system effects rapid compensation for continuing changes in feed composition which, at a fixed reaction zone temperature, otherwise adversely affect the octane rating.

3 Claims, 1 Drawing Figure

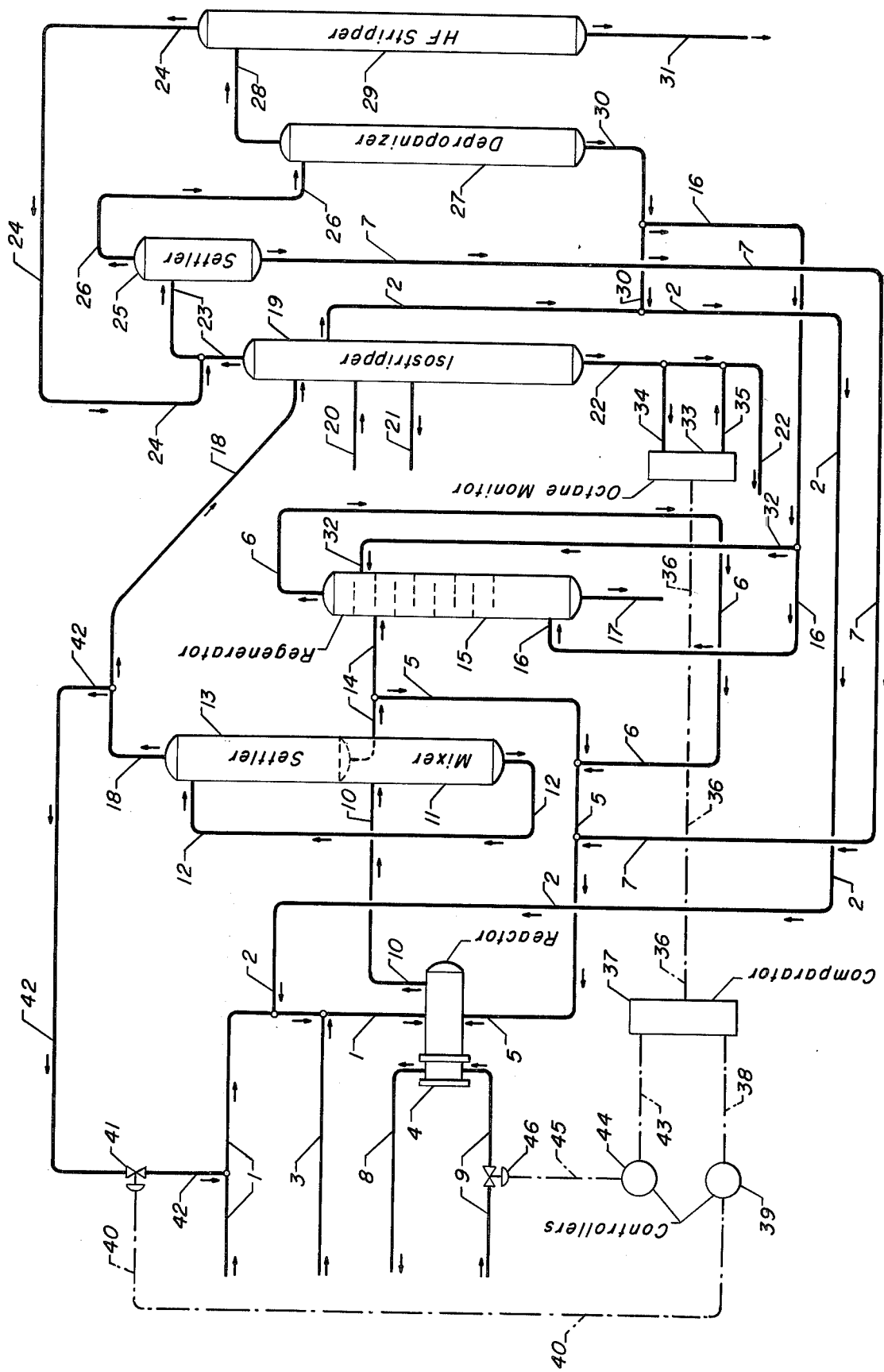

CONTROL SYSTEM FOR HF ALKYLATION

APPLICABILITY OF INVENTION

The control system herein described is intended for utilization in a process for the production of a normally liquid alkylate product via the reaction of an isoparaffin with an olefin. Although intended for use in any acid-catalyzed alkylation process — e.g. sulfuric acid alkylation — my invention is most applicable to those processes effected with a hydrogen fluoride catalyst. For more than a quarter of a century, the demand for high octane fuels, possessing enhanced anti-knock characteristics, has increased at a staggering rate. These improved fuels are required in voluminous quantities to satisfy, the ever-accelerating degree of consumption. Various processes have been developed which have proved successful in alleviating the intertwined problems attendant supply, quality and demand. Among the first of such processes was the acid-catalyzed alkylation of an isoparaffin with an olefin, both generally normally vaporous, to produce a higher molecular weight, normally liquid isoparaffin. Since isoparaffins, in contrast to normal paraffins, possess significantly higher octane ratings, and thus improve anti-knock properties, processes capable of efficiently effecting the alkylation reaction have gained wide acceptance within the petroleum industry.

For many economic and technical reasons, the alkylation process catalyzed by hydrogen fluoride catalyst appears to be preferred. HF alkylation of an isoparaffin with an olefin has, since the advent thereof, experienced a multitude of changes and improvements with respect to unit design and/or operating techniques. The control system encompassed by my inventive concept constitutes an improvement which affords enhancement of operational stability, while simultaneously providing economic advantages. Although applicable to the alkylation of an olefinic hydrocarbon having from about three to about seven carbon atoms per molecule, with an isoparaffin having from about four to about seven carbon atoms per molecule, the present control system is uniquely advantageous in those processes where isobutane is alkylated with an olefinic feed stream containing at least two olefins selected from the group consisting of propylene, 1-butene, 2-butene and isobutylene. Therefore, in the interest of brevity, further description of the present control system will be directed toward the HF-catalyzed alkylation of isobutane with mixed olefins having three or four carbon atoms per molecule. Many processes integrated into a single petroleum refining operation result in product streams containing significant quantities of lower molecular weight olefinic hydrocarbons. Principal among such processes is the well known fluid catalytic cracking process; others include thermal cracking, or pyrolysis units, coking operations and visbreaking. The olefinic feed streams are generally recovered by way of gas concentration facilities which are specifically intended to concentrate the $C_3$- and $C_4$-olefins. Exemplary of such mixed olefin concentrates, recovered from one or more of the indicated processes, is one containing about 51.3% by volume propylene, 48.2% by volume of mixed butylenes and about 0.5% by volume of mixed amylenes.

Investigations have indicated that the quality of the liquid alkylate product is, at a given reaction zone pressure, dependent upon the temperature at which the reaction mixture is maintained. Since the acid-catalyzed alkylation process is exothermic, temperature control of the reaction mixture, via indirect heat exchange with a suitable cooling medium, has been, and continues to be a commonly practiced technique. This relatively simple temperature control system will suffice where the feed stream is a substantially pure olefinic hydrocarbon. However, the feed stream in virtually 100% of the acid-catalyzed alkylation processes constitutes a mixture of two or more of the aforementioned olefinic hydrocarbons. This contributes a significant degree of complexity with respect to temperature control of the reaction mixture. Considering, for the sake of illustration, substantially pure olefinic feed streams, the quality of the alkylate produced from 1-butene is improved through an increase in the reaction temperature, while that produced from either 2-butene, or isobutylene is improved by a decrease in the reaction temperature. Additionally, a higher quality alkylate product is produced from a propylene feed stream at higher temperatures than those which are optimum for the alkylation of $C_4$-olefins. Since the character of the olefinic feed stream is dependent to a large extent upon the operation of other units within the overall refinery, which units are subject to their own peculiar operating parameters, the composition of the olefinic feed stream introduced into the alkylation system is constantly changing.

One popular prior art alkylation technique entails recycling a portion of the reaction zone effluent, after removal therefrom of the greater proportion of hydrogen fluoride, to the reaction zone. The principal advantage resides in a reduction in overall utility cost for the entire unit. Initially, the total reaction mixture is introduced into the lower vessel of a stacked, two-vessel system. The lower vessel serves as a mixing, or soaking zone, after which the effluent is charged to the upper vessel which functions as an acid settler. There is provided an acid phase, as a bottoms stream, substantially free from the major portion of hydrocarbon, and an upper hydrocarbon phase free from the major portion of HF. An aliquot portion of the latter, having a hydrocarbon/HF mol ratio of about 20.0:1.0 to about 50.0:1.0, is recycled to the reaction zone, generally in admixture with the olefinic feed stream. The amount so recycled is most often in the range of about 20.0 to about 100.0%, based upon the original feed stream. The hydrocarbon portion of the recycled stream is a mixture of alkylate product, unreacted isobutane and butanes. As such, it introduces an added factor which must be considered with respect to temperature control of the reaction mixture within the reaction zone. The present control system additionally compensates for the effect brought about by changes in the composition and temperature of this recycled effluent stream.

The control system of the present invention affords a method for effecting the rapid compensation of feed stream composition changes with respect to the quality of the normally liquid alkylate product. There is afforded an enhancement of the steady-state operation of the system, particularly with respect to the stability of alkylate product quality, as well as the economic advantages attendant an increase in operational efficiency.

OBJECTS AND EMBODIMENTS

A principal object of the present invention is to afford an improvement in the hydrogen fluoride-catalyzed alkylation of olefinic hydrocarbons. A corollary objective is to enhance the character of steady-state operation attendant the alkylation of a normally vaporous isoparaffin with a normally vaporous olefinic hyrocarbon to produce a normally liquid alkylate product.

A specific object of my invention involves the control of reaction zone temperature when alkylating an isoparaffin with a mixed olefinic feed stream while simultaneously recycling a portion of the alkylate product effluent to the reaction zone.

Therefore, one embodiment of my invention provides a control system for use in a process for alkylating an isoparaffin with an olefinic feed stream, to produce a normally liquid alkylate product, wherein (1) said feed stream contains at least two olefinic hydrocarbons and is contacted in admixture with a hydrogen fluoride catalyst, in a reaction zone, and (2) at least a portion of the reaction zone effluent is recycled thereto, which control system regulates the temperature within said reaction vessel, and comprises, in cooperative combination: (a) conduit means for introducing a cooling medium into said reaction zone, and for removing it therefrom, said cooling medium indirectly contacting the reaction mixture within said zone; (b) first flow-varying means for adjusting the flow of said cooling medium into said reaction zone; (c) second flow-varying means for adjusting the flow of effluent recycled to said reaction zone; (d) a hydrocarbon analyzer receiving a sample of said normally liquid alkylate product and developing an output signal representative of a composition characteristic of said sample; (e) first signal-receiving means to which said output signal is transmitted by said hydrocarbon analyzer, said first signal-receiving means in turn transmitting said signal to said first flow-varying means, whereby the flow of said cooling medium is adjusted in response to said composition characteristic; and, (f) second signal-receiving means to which said output signal is transmitted by said hydrocarbon analyzer, said second signal-receiving means in turn transmitting said signal to said second flow-varying means, whereby the flow of said recycled effluent is adjusted in response to said composition characteristic.

In another embodiment, my inventive concept encompasses a process for alkylating an isoparaffin with an olefinic feed stream, containing at least two olefins, which process comprises the steps of: (a) reacting said isoparaffin with said feed stream, in admixture with a hydrogen fluoride catalyst, in an alkylation reaction zone, at alkylating conditions resulting in a reaction product effluent containing normally liquid alkylate; (b) regulating the temperature of the reaction mixture, within said reaction zone, through indirect contact therein with a cooling medium, the flow of which is adjusted by first flow-varying means; (c) recycling at least a portion of the reaction zone effluent to said reaction zone, the flow of which is adjusted by second flow-varying means; (d) recovering said normally liquid alkylate from said product effluent; (e) introducing a sample of said alkylate into a hydrocarbon analyzer and developing therein an output signal which is representative of a composition characteristic of said sample; and, (f) transmitting said output signal to comparator means which compares the rate of change and actual value of said composition characteristic, generates a second output signal and transmits said second output signal to at least one of two signal-receiving means, the first of which transmits said signal to said first flow-varying means, whereby the flow of cooling medium is adjusted, and the second of which transmits said signal to said second flow-varying whereby the flow of said recycled effluent is adjusted, in response to said composition characteristic.

Other objects and embodiments will become apparent from the following additional description of the present inventive concept and the control system encompassed thereby. In other such embodiments, the hydrocarbon analyzer comprises a stabilized cool flame generator having a servo-positioned flame front, and the output signal generated thereby is representative of the octane number of the alkylate product sample.

PRIOR ART

Candor compels recognition and acknowledgment that the prior art is replete with a wide variety of publications, inclusive of issued patents, which are directed toward the acid-catalyzed alkylation of an isoparaffin with an olefin. This is particularly true with respect to hydrogen fluoride alkylation which traces its development over an approximate 30-year period. No attempt will be made herein to exhaustively delineate the hydrogen fluoride alkylation art; however, it is believed that a brief description of several innovations, for the purpose of illustrating the applicability of the present improvement, will serve to define the areas to which the present technique is applicable.

U.S. Pat. No. 3,560,587 (Cl. 260-683.48) describes the hydrogen fluoride alkylation of an isoparaffin/olefin mixture in a system which incorporates a reaction cooler, reaction soaker and a hydrogen fluoride acid-settler. U.S. Pat. No. 3,686,354 (Cl. 260-683.43) is fairly illustrative of a complete hydrogen fluoride alkylation process including reaction vessels, reaction effluent separation for acid recovery, and product separation for the recovery of the normally liquid alkylate. In this particular system, the alkylate product is separated into a relatively high-octane fraction and a relatively low-octane fraction, the latter being further treated with additional isoparaffin and hydrogen fluoride catalyst.

The present control system is intended for utilization in HF-catalyzed alkylation processes of the type above illustrated. The integration and utilization of control systems in a petroleum refining process is considered to be among recent technological innovations. In this respect, the published literature is slowly developing its own field of art, some of which includes issued patents. For example, U.S. Pat. No. 3,759,820 (Cl. 268-64) discloses the systematized control of a multi-reaction zone process in response to two different quality characteristics of the ultimately desired product. U.S. Pat. No. 3,649,202 (Cl. 23-253A) involves the control of reaction zone severity in response to the octane rating of the normally liquid product effluent, and is primarily directed toward the well known catalytic reforming process. Other examples of the systematized control of petroleum refining processes are found in U.S. Pat. No. 3,751,229 (Cl. 23-253A), U.S. Pat. No. 3,748,448 (Cl. 235-151.12) and U.S. Pat. No. 3,756,921 (Cl. 196-132).

As hereinbefore stated, the present control system is utilized to alleviate the problems attendant reaction zone temperature control in an acid-catalyzed alkylation process wherein an isoparaffin is alkylated with a mixed olefinic feed stream and a portion of the reaction zone effluent is recycled thereto. These difficulties, principally arising out of the utilization of an olefinic feed stream containing propylene, 1-butene, 2-butene and isobutylene do not appear to be recognized either in the appropriate alkylation art, or in the control system literature.

SUMMARY OF THE INVENTION

As hereinbefore set forth, my invention is directed toward an improvement in the control of reaction zone temperature while alkylating an isoparaffin/olefin reactant stream. Although applicable to the alkylation of isobutane with a butylene-containing feed stream, the process is also adaptable for utilization of other isoparaffinic and olefinic feed stocks. Suitable isoparaffinic hydrocarbons are those having from about four to about seven carbon atoms per molecule, including isobutane, isopentane, neopentane, one or more of the isohexanes and various branched-chain heptanes. Similarly, the olefinic reactant stream contains from about three to about seven carbon atoms per molecule, and is inclusive of propylene, 1-butene, 2-butene, isobutylene, the isomeric amylenes, hexenes and various heptenes.

The alkylation reaction mixture comprises hydrogen on fluoride catalyst, an isoparaffin and a mixed olefinic feed stream. With respect to the latter, the feed stream generally contains at least two olefinic hydrocarbons selected from the group consisting of propylene, 1-butene, 2-butene and isobutylene. Hydrogen fluoride catalyst is utilized in an amount sufficient to provide a catalyst/hydrocarbon volume ratio, within the reaction zone, of from about 0.5 to about 3.0. As a general practice, commercial anhydrous hydrogen fluoride will be charged to the alkylation system as the catalyst. It is possible to use hydrogen fluoride which contains as much as about 10.0% water; however, excessive dilution should be avoided since it tends to reduce the alkylating activity of the catalyst while introducing severe corrosion problems into the system. In order to reduce the tendency of the olefinic portion of the hydrocarbon feed stock to undergo polymerization prior to alkylation, the molar proportion of the isoparaffin to olefinic hydrocarbons is maintained at a value greater than about 1.0:1.0, up to about 20.0:1.0, and preferably from about 3.0:1.0 to about 15.0:1.0.

Alkylation reaction conditions include temperatures in the range of about 0° to about 200°F., and preferably from about 30° to about 110°F. In view of the fact that the alkylation reactions are highly exothermic, suitable means for removing heat from the reaction zone is required. In general practice, the reaction zone is designed such that it functions as an indirect heat-exchanger. A cooling medium is introduced into the reaction zone and contacts the reaction mixture therein. Generally, the quantity of cooling medium introduced is controlled by direct response to the internal temperature of the reaction mixture. While such a basic technique admittedly offers some form of temperature control, it is clearly susceptible to a relatively large cycling range. In effect, this technique maintains the reaction zone temperature above a predetermined minimum and below a predetermined maximum, the latter to avoid additional polymerization reactions which adversely affect the product quality.

Alkylation pressures are suffficiently high to maintain the hydrocarbon feed stream and hydrogen fluoride catalyst in substantially liquid phase; that is, pressures from about 15 psig. to about 600 psig. The contact time in the alkylation reaction zone is conveniently expressed in terms of a space-time relationship which is defined as the volume of catalyst within the reaction zone divided by the volume rate per minute of hydrogen reactants charged to the zone. Usually, the space-time relationship will be less than about 5 minutes and preferably less than about 2 minutes. The product effluent from the alkylation reaction zone is introduced into a separation zone generally comprising a two-vessel stacked system. The mixture is initially introduced into the lower vessel which serves as a vertical mixer, or soaking zone. The mixer is sized and designed to provide an average residence time in the range of about 60 to about 1200 seconds. After the desired residence time, the effluent is introduced into the upper vessel which serves as a settler to provide a hydrocarbon stream substantially free from the major portion of hydrogen fluoride, and a settled hydrogen fluoride phase substantially free from the major proportion of hydrocarbons. In accordance with a relatively recent technique, at least a portion of the reaction zone effluent (the hydrocarbon stream) is emulsified and recycled to the alkylation reaction zone, in an amount of from 20.0 to about 100.0%, based upon the original feed stream plus recycle. The settled hydrogen fluoride is recycled to the reaction zone in admixture with regenerated hydrogen fluoride. The reaction zone effluent generally contains a minor proportion of polymer products nothwithstanding temperature control of the reaction mixture. In order to prevent the build-up of polymer products within the system, a relatively minor proportion of the settled hydrogen fluoride phase is introduced into an acid regenerator. Hydrogen fluoride recovered therefrom is recycled to the alkylation reaction zone.

That portion of the hydrocarbon phase separated in the settler vessel and not recycled to the reaction zone, is introduced into an isostripper fractionating column for the recovery of the normally liquid alkylate product. Propane, unreacted isobutane and a minor quantity of hydrogen fluoride catalyst are removed as an overhead stream and introduced into a separate settling zone, from which the hydrogen fluoride is recycled to the reaction zone. The hydrocarbon phase from this settler is introduced into a depropanizng column, with isobutane being removed as a bottoms fraction, recycled in part to the reaction zone and in part to the acid-regenerator for the purpose of stripping hydrogen fluoride from the polymer products which are removed as a bottoms phase. A principally vaporous phase, predominantly propane, and containing a minor quantity of hydrogen fluoride, is introduced into a hydrogen fluoride stripping column. The hydrogen fluoride is removed as an overhead fraction and introduced into the isostripper settler for ultimate return to the reaction zone. Propane is removed from the bottom of the hydrogen fluoride stripper and sent to storage; this stream is generally subjected to both alumina treating and potassium hydroxide treating to remove trace quantities of hydrogen fluoride. Similarly, although the normally liquid alkylate product is generally recovered substantially free from hydrogen fluoride, cautious operating techniques dictate that the same be subjected to similar treatments.

The foregoing is representative of a typical hydrogen fluoride alkylation process. As previously stated, the present control system is intended for integration into such a unit for the purpose of achieving a greater degree of efficiency with respect to reaction zone temperature control, accompanied by an enhancement of the steady-state operation of the entire system. As previously stated, the character of the olefinic feed stream to an HF alkylation unit is generally dependent upon the operation of other processes within the refinery. Since these other processes are subjected to their own peculiar operating parameters, the composition of the olefinic feed stream is constantly changing. This contributes a particular problem with respect to temperature control of the alkylation reaction zone mixture. Considering only propylene, 1-butene, 2-butene and isobutylene, the normally liquid alkylate product quality is improved by increasing the reaction temperature, with respect to 1-butene, and by decreasing the temperature of the reaction mixture with respect to 2-butene and isobutylene. This anomaly is further compounded by virtue of the fact that a higher quality alkylate product results from a propylene feed stream processed at higher tempertures than those which are considered optimum for the alkylation of $C_4$-olefins.

As hereinbefore stated, a portion of the hydrocarbon phase recovered as an overhead stream from the settler, is recycled to the reaction zone. Although the hydrocarbon portion of this recycle stream is constantly changing, in view of the changes in the original olefinic feed stream to the unit, the hydrocarbon/HF mol ratio thereof will generally be in the range of about 20.0:1.0 to about 50.0:1.0. Recycling this mixture of alkylate product, unreacted isobutane and butanes introduces an added factor to be considered with respect to temperature control of the reaction mixture within the reaction zone. Through the use of the present control system, there is afforded additional compensation for the effect brought about by changes in the composition and temperature of this recycled effluent stream.

In accordance with the present invention, a hydrocarbon analyzer is employed to receive a sample of the normally liquid alkylate product removed as a bottoms stream from the isostripping column. An output signal, which is representative of a composition characteristic of the sample, is developed by the hyrocarbon analyzer. This output signal is transmitted to signal-receiving means, or controller means, the latter in turn transmitting the signal to flow-varying means whereby the flow of the cooling medium into the alkylation reaction zone is adjusted and the flow of recycled reaction zone effluent is adjusted, both in response to the varying composition characteristic. In a preferred embodiment, the output signal is initially transmitted to comparator means which compares the rate of change and actual value of said composition characteristic, generates a second output signal and transmits said second signal to at least one of the controller means, in order to regulate either the flow of cooling medium, or the flow of recycled effluent, or both. Complete details of the hydrocarbon analyzer, intended for utilization as an essential element of the present control system may be obtained upon reference to U.S. Pat. No. 3,463,613 (Cl. 23-230).

As stated therein, a composition characteristic of a hydrocarbon sample can be determined by burning the same in a combustion tube under conditions generating a stabilized cool flame. The position of the flame front is automatically detected and employed to develop a signal which, in turn, is utilized to vary a combustion parameter such as combustion pressure, induction zone temperature or air flow, in a manner which immobilizes the flame front regardless of changes in the composition characteristic of the hydrocarbon sample. The change in the combustion parameter, required to immobilize the flame front following a change of sample composition, is, therefore, corollatable with the composition characteristic change. An appropriate readout device, of the type well known in the appropriate art, connecting with the hydrocarbon analyzer, may be calibrated in terms of the desired identifying characteristic as, for example, the octane rating.

The hydrocarbon analyzer is characterized as comprising a stabilized cool flame generator having a servopositioned flame front. The type of analysis affected thereby is not a compound-by-compound analysis such as that presented by instruments including mass spectrometers and vapor-phase chromatographs. On the contrary, the analysis is represented by a continuous output signal which is responsive to and indicative of hydrocarbon composition and, more specifically, is corollatable with one or more conventional identifications or specifications of petroleum products including Reid vapor pressure, ASTM or Engler distillations, or, for motor fuels, anti-knock characteristics such as research octane number, motor octane number, or a composite thereof.

The hydrocarbon analyser receives a hydrocarbon sample (preferably continuously) containing predominately gasoline boiling range components; the output signal provides a direct measure of octane number. For brevity, the hydrocarbon analyzer is herein referred to as "an octane monitor".

The control system will further include comparator means which initially receives the output signal from the hydrocarbon analyzer, and compares the rate of change and actual value of the composition characteristic with previously received values. A second output signal is generated and transmitted to the signal-receiving means, or flow controllers, to reset the set points thereof in response to successive comparisons of the composition characteristic. The flow control means in turn transmit the signal to the flow-varying means, whereby the flow of the cooling medium and the flow of the effluent recycle stream is adjusted in response thereto. Where desired, second comparator means can be included for comparing the actual value of the composition characteristic with previously determined deviation limits and for generating an adjustment output signal in response to this comparison. When the value lies beyond the set limits, and the rate of change with respect to time indicates that the value will continue to depart from such limits, the second comparator means will generate an adjustment signal to alter the rate of change. Details of comparator means, as utilized in a control system for a reaction process, may be found in U.S. Pat. No. 3,748,448 (Cl. 235-151.12).

In further describing my invention, reference will be made to the accompanying drawing which is presented for the sole purose of illustrating a typical prior art HF alkylation process having integrated therein the control system of the present invention. In the drawing, the process is presented by way of a simplified flow diagram in which details such as pumps, instrumentation and other controls, quench systems, heat-exchange and heat-recovery circuits, valving, start-up lines and similar hardware have been eliminated as non-essential to an understanding of the techniques involved. The use of such miscellaneous appurtenances, to modify the process as illustrated, will be evident to those possessing the requisite skill in the art of petroleum refining technology.

DESCRIPTION OF DRAWING

The drawing will be described in conjunction with a commercially-scaled unit designed for the alkylation of isobutane with a mixed olefin feed stream, containing propylene, various butylenes and amylenes, in an exchanger-type reaction vessel. The olefinic charge stream, in the amount of about 5,482 Bbl./day, enters the process via line 1; make-up isobutane is introduced via line 3; and, field butane, in the amount of 923 Bbl./day is introduced into the system via line 20, the isobutane-rich portion thereof being recycled by way of line 2 to combine with the olefinic hydrocarbon and make-up isobutane mixture in line 1. Also introduced into the reactant mixture is a portion of the reaction zone effluent (8,316.66 mol/hr.) via line 42, the source of which is hereinafter described. That this recycle stream is shown as being combined with the olefinic feed stream in line 1 is not essential to the present invention; that is, it could be shown as initially combining with the make-up isobutane being introduced via line 3. In any event, the entire reactant mixture continues through line 1, being introduced thereby into reactor 4. From thee fresh feed charge streams, it is desired to produce a full boiling range, normally liquid alkylate product having a Reid vapor pressure of about 10.0 lbs. and a clear octane rating of about 93.0.

With specific reference now to the drawing, 5,482 Bbl./day of the olefinic feed stream (884.45 mols/hr.), is introduced into the process through line 1, and is admixed with 49,878 Bbl./day (7,107.45 mols/hr.) of an isobutane rich recycle stream in line 2, containing 107.16 mols of HF acid; 2,452 Bbl./day (347.65 mols/hr.) of make-up isobutane (95.0% by volume) is introduced via line 3 and 8,316.66 mols/hr. of recycled effluent via line 42, containing 212.78 mols/hr. of HF acid. The mixture continues through line 1 into alkylation reactor 4 which is designed to function as a heat-exchanger having multiple feed injection points, which technique is well known and not, therefore, illustrated herein. Hydrogen fluoride, in an amount of 88,360 Bbl./day (54,255.23 mols/hr.), is recycled from settler 13 into reactor 4 by way of line 5. This stream is inclusive of 169.95 mols/hr. of regenerated acid from line 6, also containing 297.31 mols/hr. of an isobutane-rich stream and 107.16 mols/hr. of settled HF acid recovered in line 7 as hereinafter described. In reactor 4, the isobutane/olefinic hydrocarbon mol ratio is about 13.0:1.0 and the HF acid/hydrocarbon volumetric ratio is about 1.48:1.0, exclusive of the recycle stream in line 42. Reactor 4 is maintained at a pressure of about 233 psig., with the HF acid and reactant stream being introduced at a temperature of about 100°F. The material balance around reaction zone 4, exclusive of the HF acid stream, is presented in the following Table I, with the concentrations of the various components being given in terms of mols/hr. for convenience.

TABLE I

| Component | Reaction Zone Material Balance Charge | Effluent |
| --- | --- | --- |
| Ethane | 0.92 | 0.92 |
| Propylene | 271.49 | — |
| Propane | 583.58 | 599.71 |
| Butylenes | 256.25 | — |
| Isobutane | 6896.52 | 6352.38 |

TABLE I-continued

| Component | Reaction Zone Material Balance Charge | Effluent |
| --- | --- | --- |
| N-Butane | 505.62 | 510.36 |
| Amylenes | 2.76 | — |
| Isopentane | 80.45 | 98.88 |
| N-Pentane | 0.59 | — |
| Hexane-plus | 37.85 | 541.63 |
| Polymer Products | — | 0.17 |

As hereinbefore set forth, HF alkylation of an isoparaffin/olefin reactant mixture is highly exothermic, and must be tempered through the use of a cooling medium. In the illustration, the exothermic heat of reaction is removed through the use of 8,017 gallons per minute of water (about 85°F.) entering via line 9, and exiting via line 8 at a temperature of about 90°F. The total reaction product effluent is withdrawn through line 10 at a temperature of about 100°F. and a pressure of about 218 psig.

The product effluent continues through line 10 into mixer/soaker 11 wherein it is maintained for an effective residence time of about 8 minutes. After this holding period, the product effluent is transferred via line 12 into HF acid settler 13. Settled HF acid is removed via line 14 in the amount of 88,013 Bbl./day (54,040.62 mols/hr.), at a pressure of about 203 psig. Of this amount, 87,735 Bbl/day (53,870.77 mols/hr.) are diverted through line 5 as acid recycle to reactor 4. Generally, the remaining 278 Bbl/day (169.95 mols/hr.) is accumulated until a sufficient quantity is available for introduction via line 14 into acid regenerator 15. Regenerator 15 functions at a bottom pressure of about 155 psig., a bottom temperature of about 350°F., a top pressure of about 145 psig. and a top temperature of about 160°F. HF acid is stripped from polymer products by the introduction, via line 16, of an isobutane-rich stream (212.22 mols/hr.), at a temperature of 450°F. and a pressure of about 160 psig. Polymer products, in the amount of about 3.2 Bbl./day (0.17 mols/hr.) are recovered through line 17, at a pressure of about 155 psig. and a temperature of about 350°F. A portion of the isobutane-rich stream from line 16 is diverted through line 32 in the amount of about 85,09 mols/hr., cooled to a temperature of about 100°F., and introduced as reflux into acid regenerator 15. The overhead stream in line 6, comprising 297.31 mols/hr. of hydrocarbons and 169.95 mols/hr. of regenerated HF acid, is recycled to combine with the settled acid in line 5, and returned to reactor 4. The material balance with respect to acid regenerator 15 is presented in the following Table II:

TABLE II

| Component | Acid Regenerator Material Balance Line Number | | | | |
| --- | --- | --- | --- | --- | --- |
| | 14 | 32 | 16 | 6 | 17 |
| Propane | — | 1.00 | 6.46 | 7.46 | — |
| Isobutane | — | 78.66 | 198.82 | 277.48 | — |
| N-Butane | — | 4.91 | 6.45 | 11.36 | — |
| Isopentane | — | 0.52 | 0.48 | 0.99 | — |
| HF Acid | 169.95 | — | — | 169.95 | — |
| Polymers | 0.17 | — | — | — | 0.17 |

The hydrocarbon-rich phase from settler 13, at a temperature of about 100°F. and a pressure of about 203 psig., is withdrawn through line 18 in an amount of 16,633.32 mols/hr., of which 425.56 mols/hr. is HF acid. About 50.0% of this hydrocarbon-rich phase is diverted via line 42 to be combined with the olefinic feed stream in line 1. The remainder, consisting of 8,103.88 mols/hr. of hydrocarbons and 212.78 mols/hr. of HF acid, is heated to a temperature of about 170°F. and introduced into isostripper 19 at a pressure of about 152 psig. Field butane, at a temperature of about 100°F., enters the upper section of isostripper 19 through line 20, in an amount of 133.07 mols/hr. A normal butane-rich stream, in the amount of 89.16 mols/hr., is recovered as a side-cut via line 21, and is subjected to treatment with potassium hydroxide for the removal of trace quantities of HF acid. Isostripper 19 functions at a bottom temperature of about 371°F., a bottom pressure of about 160 psig., a top temperature of about 140°F. and a top pressure of about 152 psig. The normally liquid alkylate product is recovered through line 22 in an amount of about 5,932 Bbl./day (579.97 mols/hr.), and is also subjected to caustic treating for acid removal. An isobutane-rich stream, in the amount of 6,897.43 mols/hr., including 19.42 mols/hr. of a pump flush stream (not illustrated) from depropanizer 27, is recycled via lines 2 and 1 to reactor 4. Also recovered in line 2 is HF acid in the amount of 107.16 mols/hr. Overhead vapors, consisting of 1,380.08 mols/hr. of hydrocarbons and 120.85 mols/hr. of HF acid, is withdrawn through line 23.

Of this amount, 690.04 mols/hr. of hydrocarbons and 13.69 mols/hr. of HF are utilized as reflux to isostripper 19; the composition of the hydrocarbon phase is about 0.91 mols of ethane, 166.55 mols of propane, 495.23 mols of isobutane, 24.92 mols of N-butane and 2.44 mols of isopentane. The component composition of the various charge and effluent streams, exclusive of HF acid, are presented in the following Tables III and IV:

A portion of the overhead from line 23 is diverted as reflux to the top of isostripper 19; this portion consists of 690.04 mols/hr. of hydrocarbons and 13.69 mols/hr. of HF. The remainder is admixed with 14.05 mols/hr. of HF from line 24, and is introduced into settler 25. Settled acid, in the amount of 107.16 mols/hr., is recycled to reactor 4 by way of line 7 and 5. Hydrocarbons, in the amount of 703.11 mols/hr., and HF acid, in the amount of 14.05 mols/hr., are introduced via line 26 into depropanizer 27. A propane concentrate, containing 14.05 mols/hr. of HF acid is recovered as an overhead stream in line 28 being introduced thereby into HF stripper 29.

TABLE III

| Component | Isostripper Feed Streams | |
|---|---|---|
|  | Line 18 | Line 20 |
| Ethane | 0.92 | — |
| Propylene | — | — |
| Propane | 599.71 | 3.10 |
| Butylenes | — | — |
| Isobutane | 6352.38 | 62.63 |
| N-Butane | 590.72 | 64.99 |
| Isopentane | 98.88 | 1.52 |
| N-Pentane | — | 0.83 |
| Hexane-plus | 541.63 | — |

TABLE IV

| Component | Isostripper Effluent Streams | | | |
|---|---|---|---|---|
|  | Line 23 | Line 2 | Line 21 | Line 22 |
| Ethane | 1.83 | — | — | — |
| Propylene | — | — | — | — |
| Propane | 336.11 | 412.71 | — | — |
| Butylenes | — | — | — | — |
| Isobutane | 987.75 | 5935.17 | 4.30 | 1.17 |
| N-Butane | 49.54 | 418.35 | 83.28 | 50.23 |
| Isopentane | 4.84 | 72.59 | 1.52 | 24.01 |
| N-Pentane | — | — | — | 0.69 |
| Hexane-plus | — | 37.85 | 0.06 | 503.72 |

The bottoms stream, in an amount of 540.03 mols/hr., is withdrawn through line 30 and utilized as follows: 32.74 mols/hr. are employed as a pump flush stream (not illustrated); 297.31 mols/hr. are diverted through line 16 for use in acid regenerator 15; and, 210.02 mols/hr. continue through line 30 for recycle to reactor 4 via line 2. Depropanizer 27 functions with a bottom pressure of about 315 psig., a bottom temperature of about 220°F., a top temperature of about 140°F. and a top pressure of about 305 psig. The material balance for depropanizer 27 is presented in the following Table V:

TABLE V

| Component | Depropanizer Material Balance | | |
|---|---|---|---|
|  | Line 26 | Line 28 | Line 30 |
| Ethane | 0.92 | 0.92 | — |
| Propane | 169.72 | 159.40 | 10.31 |
| Isobutane | 504.63 | 2.74 | 501.88 |
| N-Butane | 25.38 | — | 25.38 |
| Isopentane | 2.48 | — | 2.48 |

Hydrogen fluoride, in an amount of about 14.05 mols/hr. is withdrawn as an overhead stream in line 24, and admixed with the isostripper overhead in line 23. The 163.07 mols/hr. of hydrocarbons are recovered via line 31. HF stripper 29 functions with a top temperature of about 140°F., and a pressure of about 310 psig. and a bottoms temperature of 150°F., and a pressure of about 320 psig.

The normally liquid alkylate product, withdrawn via line 22 has a Reid Vapor Pressure of about 9.9 lbs., a clear octane rating of about 93.3 (research method), 104.2 with 3.0 cc. of tetraethyl lead, and a gravity of 74.6 °API. The results of a 100 ml. ASTM distillation are presented in the following Table VI:

TABLE VI

| Alkylate Product ASTM Distillation | |
|---|---|
| Volume Percent | °F. |
| Initial Boiling Point | 92 |
| 5.0% | 119 |
| 10.0% | 136 |
| 20.0% | 170 |
| 30.0% | 196 |
| 40.0% | 206 |
| 50.0% | 212 |
| 60.0% | 218 |
| 70.0% | 223 |
| 80.0% | 234 |
| 90.0% | 273 |
| 95.0% | — |
| End Boiling Point | 356 |

Octane monitor 33 is field-installed adjacent isostripper 19; it utilizes a stabilized cool flame generator having a servo-positioned flame front. The flow of oxidizer (air) and fuel (alkylate product effluent from line 22) are fixed, as is the induction zone temperature. Combustion pressure is the parameter which is varied in such manner that the stabilized cool flame front is immobilized.

Upon experiencing and detecting a change in a composition characteristic, in this illustration octane number, the change in pressure required to immobilize the flame front within octane monitor 33 provides a direct indication of the change in the sample delivered to the analyzer's combustion chamber by way of line 34. Typical operating conditions for the octane monitor are: air flow, 3,500 cc./min. (STP); fuel flow, 1.0 cc./min.; induction zone temperature, Research Octane, 700°F.; induction zone temperature, Motor Octane, 800°F.; combustion pressure, 4.0 to 20.0 psig.; and, octane range (max.), 80 to 102. The actual calibrated span of the octane monitor as herein employed, will generally be narrower. For example, where the target octane rating is 95.0 Clear (Research Method), a suitable span may be 90–96 research octane. When such a relatively narrow span is employed, the octane number change is essentially directly proportional to the change in combustion pressure. As shown in the drawing, the sample system may comprise a sample loop taking, for example, liquid at a rate of about 100 cc./min. via line 34 and returning it by way of line 35, the sample itself being injected, from an intermediate point, at a controlled rate by a metering pump to the combustion tube of the octane monitor.

The octane monitor output signal is transmitted through line 36 to ultimately reset the set point of controllers 39 and 44. The latter will then make the appropriate adjustments, by way of lines 40 and 45, in control valves 41 and 46, either to decrease, or increase the flow rates of the effluent recycle in line 42, and of the cooling medium in line 9. It is understood, of course, that control valve 46 can be installed in line 8, the cooling medium exit line from reaction zone 4. In a preferred technique, the octane monitor output signal is transmitted via line 36 into comparator means 37, and therefrom through lines 38 and 43 into controllers 39 and 44. Since the sample of alkylate product from line 22 is taken continuously, and a varying output signal is continuously being transmitted via line 36, rapid compensation for the changes in the olefinic composition of the feed stream in line 1 is afforded. Additionally, the effect of effluent recycle via line 42 is readily offset. Comparator 37 is capable of functioning to change either the flow of cooling medium through line 9, the flow of recycled effluent in line 42, or both. By checking the current output signal, received via line 36, against the previous signal, comparator 37 transmits the proper signal or signals to controllers 39 and 44 to correct for any indicated difference.

To illustrate further, it will be presumed that the olefinic feed stream composition changes to the extent that there is a decrease in the content of 1-butene, in which case the reaction zone temperature is too high, and an increase in the propylene content greater than the change in $C_4$-olefins, in which case the temperature is too low. Octane monitor 33 senses the decreasing octane rating of the alkylate product and transmits a corresponding output signal through line 36 to comparator 37. The latter compares and checks this current signal against the previous signal and transmits output signals via lines 43 and 38 to controllers 44 and 39, in order to correct the difference and reset the control points. The controllers in turn cause valves 46 and 41 to close such that the flow of cooling medium and effluent recycle is decreased, and the reaction zone temperature increased. When the ultimate effect is sensed by octane monitor 33, comparator 37 will compare and check the then current output signal, and make the appropriate change, or changes required to achieve the target octane number.

Through the utilization of the present control system, a refiner functioning with a mixed olefin feed stream, as the charge to an HF alkylation system, is afforded close control over either a desired target octane rating, or over maximizing the octane rating, regardless of the changes in feed composition.

I claim as my invention:

1. For a process for alkylating an isoparaffin with an olefinic feed stream, to produce a normally liquid alkylate product, wherein (1) said feed stream contains at least two olefinic hydrocarbons and is contacted in admixture with a hydrogen fluoride catalyst, in a reaction zone, and (2) at least a portion of the reaction zone effluent is recycled thereto, the control system, for regulating the temperature within said reaction zone, which comprises, in cooperative combination:
   a. conduit means for introducing a cooling medium into said reaction zone, and for removing it therefrom, said cooling medium indirectly contacting the reaction mixture within said zone;
   b. first flow-varying means for adjusting the flow of said cooling medium into said reaction zone;
   c. second flow-varying means for adjusting the flow of effluent recycled to said reaction zone;
   d. a hydrocarbon analyzer receiving a sample of said normally liquid alkylate product and developing an output signal representative of a composition characteristic of said sample;
   e. first signal-receiving means to which said output signal is transmitted by said hydrocarbon analyzer, said first signal-receiving means in turn transmitting said signal to said first flow-varying means, whereby the flow of said cooling medium is adjusted in response to said composition characteristic; and,
   f. second signal-receiving means to which said output signal is transmitted by said hydrocarbon analyzer, said second signal-receiving means in turn transmitting said signal to said second flow-varying means, whereby the flow of said recycled effluent is adjusted in response to said composition characteristic.

2. The control system of claim 1 further characterized in that said hydrocarbon analyzer comprises a stabilized cool flame generator having a sevo-positioned flame front.

3. The control system of claim 1 further characterized in that said output signal is transmitted to comparator means which compares the rate of change and actual value of said composition characteristic, generates a second output signal and transmits said second signal to at least one of said signal-receiving means.

* * * * *